United States Patent
Ekeberg et al.

(10) Patent No.: US 12,409,287 B2
(45) Date of Patent: Sep. 9, 2025

(54) TRACHEOSTOMY VALVE COMPRISING A FLEXIBLE MEMBRANE

(71) Applicant: FOGLESS INTERNATIONAL AB, Jönköping (SE)

(72) Inventors: Daniel Ekeberg, Jönköping (SE); Inge Blomquist, Vaggeryd (SE)

(73) Assignee: FOGLESS INTERNATIONAL AB, Jönköping (SE)

( * ) Notice: Subject to any disclaimer, the term of this patent is extended or adjusted under 35 U.S.C. 154(b) by 803 days.

(21) Appl. No.: 17/292,033

(22) PCT Filed: Oct. 23, 2019

(86) PCT No.: PCT/SE2019/051043
§ 371 (c)(1),
(2) Date: May 7, 2021

(87) PCT Pub. No.: WO2020/096503
PCT Pub. Date: May 14, 2020

(65) Prior Publication Data
US 2021/0393909 A1  Dec. 23, 2021

(30) Foreign Application Priority Data
Nov. 9, 2018 (EP) .................................. 18205318

(51) Int. Cl.
*A61M 16/04* (2006.01)
*A61M 16/20* (2006.01)

(52) U.S. Cl.
CPC ...... *A61M 16/0468* (2013.01); *A61M 16/208* (2013.01)

(58) Field of Classification Search
CPC ........... A61M 16/0463; A61M 16/0465–0468; A61M 16/20–209; A61M 2205/42; A61M 2202/0208

(Continued)

(56) References Cited

U.S. PATENT DOCUMENTS 7,025,784 B1   4/2006  Blom et al.
10,391,273 B2*  8/2019  Nussbaum ........ A61M 16/0666
(Continued)

FOREIGN PATENT DOCUMENTS

CN  103189092 A   7/2013
CN  107261286 A   10/2017
(Continued)

OTHER PUBLICATIONS

International Search Report and Written Opinion mailed mailed Jan. 27, 2020; International Patent Application No. PCT/SE2019/051043 filed on Oct. 23, 2019. ISA/SE.
(Continued)

*Primary Examiner* — Elliot S Ruddie
(74) *Attorney, Agent, or Firm* — McDonald Hopkins LLC

(57) ABSTRACT

The present invention relates to a tracheostomy valve configured to be in fluid communication with a patient's trachea. The valve comprising a hollow valve body, a flexible membrane adapted to work as a check valve opening the valve when the patient inhales and sealingly closing the valve when the patient exhales, and a cap with at least one through hole making the cap fenestrated. The hollow valve body having a through hole forming a passageway for fluid extending between an inner end being an outlet of the hollow valve body and an outer end being an inlet of the hollow valve body. The fenestrated cap being configured to be detachably attached to the outer valve body end, and the inner valve body end is configured to be in fluid communication with the patient's trachea.

6 Claims, 7 Drawing Sheets

(58) Field of Classification Search
USPC .................................... 128/207.14–207.17
See application file for complete search history.

(56) References Cited

U.S. PATENT DOCUMENTS

| | | | |
|---|---|---|---|
| 2004/0123868 A1 | 7/2004 | Rutter | |
| 2006/0260703 A1 | 11/2006 | Johnson | |
| 2009/0032028 A1* | 2/2009 | Bare .................. | A61M 16/208 |
| | | | 128/207.16 |
| 2014/0305440 A1 | 10/2014 | Root | |
| 2015/0083119 A1 | 3/2015 | Persson | |
| 2015/0136137 A1 | 5/2015 | Bugamelli et al. | |
| 2015/0238718 A1* | 8/2015 | Schnell .................... | A61F 2/20 |
| | | | 128/205.27 |
| 2016/0074682 A1 | 3/2016 | Kudav | |

FOREIGN PATENT DOCUMENTS

| | | | | |
|---|---|---|---|---|
| DE | 202013009823 U1 | 2/2014 | | |
| EP | 1377334 | 1/2004 | | |
| EP | 1747792 A1 | 1/2007 | | |
| EP | 2501424 A1 | 9/2012 | | |
| WO | WO-02074377 A1 * | 9/2002 | ........ | A61M 16/0468 |
| WO | 2009018384 A1 | 2/2009 | | |
| WO | 2011062533 | 5/2011 | | |
| WO | WO-2011062533 A1 * | 5/2011 | ........ | A61M 16/0468 |
| WO | 2015067234 A2 | 5/2015 | | |

OTHER PUBLICATIONS

European Search Report mailed Feb. 4, 2019; European Patent Application No. 18205318.1.

* cited by examiner

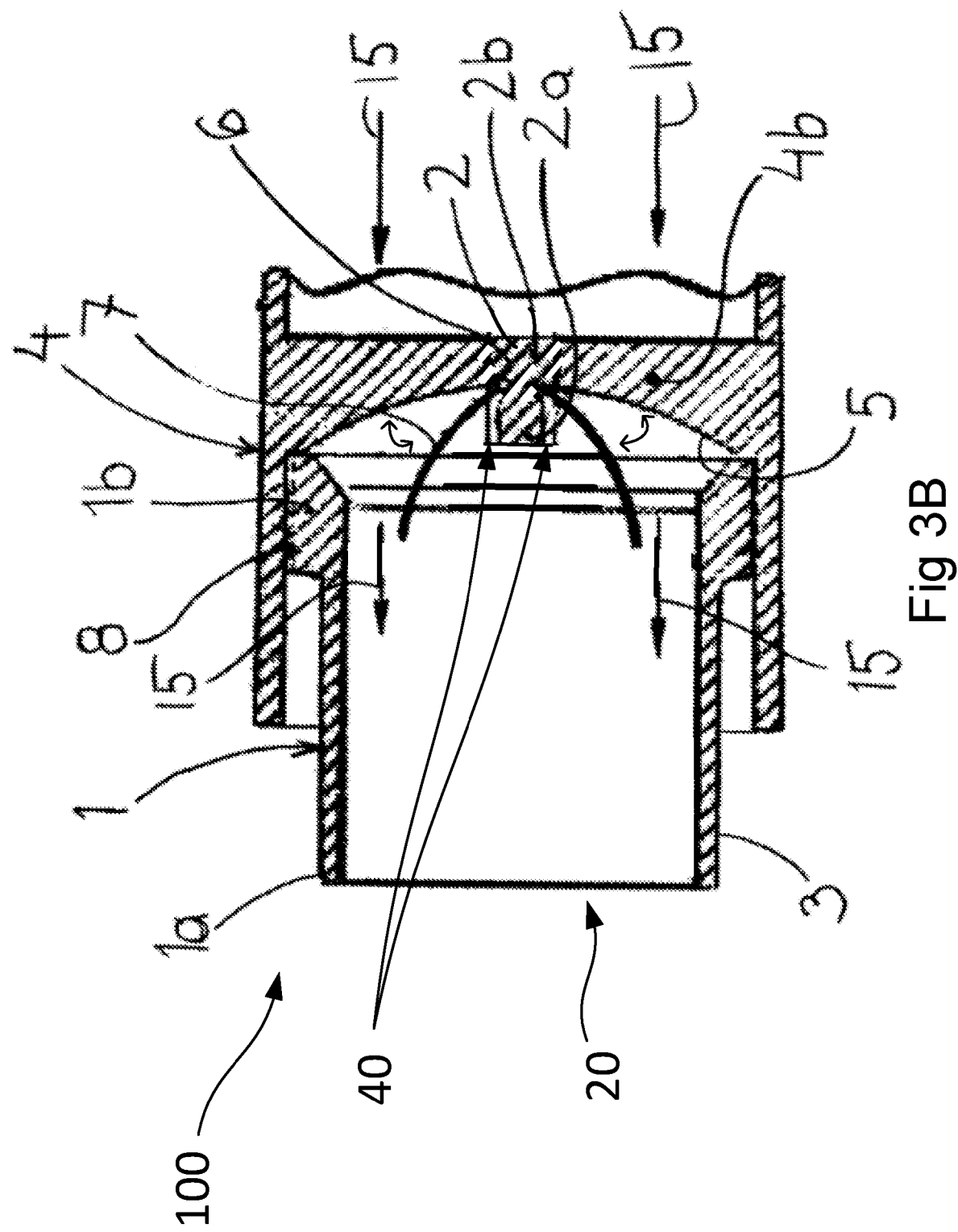

TRACHEOSTOMY VALVE COMPRISING A FLEXIBLE MEMBRANE

CROSS-REFERENCE TO RELATED APPLICATION

This application is a 35 U.S.C. § 371 national stage application of PCT Application No. PCT/SE2019/051043 filed on Oct. 23, 2019, entitled "TRACHEOSTOMY VALVE COMPRISING A FLEXIBLE MEMBRANE," which claims priority to European Patent Application No. 18205318.1 filed on Nov. 9, 2018, each of which are incorporated herein in their entirety by reference.

TECHNICAL FIELD

The present invention relates to a tracheostomy valve intended to be attached at the end of a tracheostomy tube in order to regulate airflow through the tube. The valve closes or is kept closed when the patient with the tracheostomy valve exhales (and possibly speaks) and opens and is kept open only when the patient inhales, allowing air to flow through the tracheostomy valve and through the tracheotomy tube to the patients lungs.

BACKGROUND ART

Different types of solutions for breathing valves including membranes are known within the above area. Many of these valves also improve the ability to speak.

Examples of such valves are disclosed in WO 2009/018384 and EP 2 501 424 B1 disclosing tracheostomy valves comprising valve bodies having first inner ends, second outer ends, and passageways extending between the ends through the valve bodies to allow air flow from and through the first to the second ends. Outer in this context means facing away from a patient (from a tracheostomy tube) and inner means facing the patient, i.e. the first inner ends are attachable to the tracheostomy tube. Transverse flexible membranes are located within the passageways at a distance from the first ends of these valves. Caps are adapted to be secured to the outer valve ends and have openings with diameters largely corresponding to the inner diameters of passageways, the openings defining rims. Each cap is provided with a hub and radial spokes extend from the hub to the rim. The hub is provided with a hole designed to mate with a post on a rib located in the passageway transversely to the direction of airflow through the passageway near the outer end. The post is located at the centre of the rib on the outer rib side. This post cooperate with a central hole in the membrane to hold the membrane in place. The rib has a slightly raised portion adjoining the post. The rim is provided with a seating ring on the inner side (i.e. the side facing the patient when the cap is mounted) for supporting the periphery of the membrane. When the cap is attached, the central part of the membrane will be clamped between the hub and the raised portion on the rib. The seating ring is offset inwards relative to the inner surface of the hub.

In these exemplary valves, when the cap is attached, each flexible membrane is deformed so as to be preloaded into engagement with the seating ring intended to result in an un-interrupted positive seal between membrane and seating ring.

SUMMARY OF THE INVENTION

The object of the present invention is to obtain a tracheotomy valve of the general kind described above, which opens immediately upon inhalation and which closes immediately and positively at the end of inhalation. The airflow through the valve also should be optimized. The valve should remain closed and sealed during exhalation and should not open until the next inhalation. One reason that this is important is to allow the patient to speak clearly. It is also desirable that the opening and the closing of the valve is fast and substantially noiseless. The valve as such also should minimize noise.

This object is achieved with a tracheostomy valve as set forth in the appended claims.

One advantage is that the membrane of the valve is flexed/bent when both opening and closing the valve with a controlled and well-defined movement according to the invention.

An advantage of the invention is that the bending of the membrane of the valve is done similar to bending two wings or sections or segments about either sides of a straight but non-existing virtual beam in only one plane when opening the valve for intake of air is enabled by shaping the inner surface of the valve by means of vaulting or arching or cambering or making it curved or rounded or bent, such that the membrane gets a certain preload/bias/prestress and a pre-defined start of its movement by being opened in two segments, whereby a lower pressure drop or less resistance against opening is achieved.

Another advantage of the invention is that the bending of the membrane of the valve is done similar to bending two wings or sections or segments about either sides of a straight but non-existing virtual beam in only one plane when opening the valve for intake of air is enabled by shaping the inner surface of the valve by means of vaulting or arching or cambering or into a curved or rounded or bent shape, such that the membrane gets a certain preload or bias or prestress and a pre-defined and secure and repeatable/reproducible movement by being opened in two segments, whereby the valve opens and closes much easier, quicker and with less noise compared to prior art.

Generally, all terms used in the claims are to be interpreted according to their ordinary meaning in the technical field, unless explicitly defined otherwise herein. All references to "a/an/the [element, device, component, means, etc.]" are to be interpreted openly as referring to at least one instance of said element, device, component, means, etc., unless explicitly stated otherwise. Further, by the term "comprising" it is meant "comprising but not limited to" throughout the application.

BRIEF DESCRIPTION OF THE DRAWINGS

The foregoing will be apparent from the following more particular description of the example embodiments, as illustrated in the accompanying drawings in which like reference characters refer to the same parts throughout the different views. The drawings are not necessarily to scale, emphasis instead being placed upon illustrating the example embodiments.

FIGS. 3A and 3B illustrate the function of the valve, i.e. FIG. 3A shows the valve in its closed state and FIG. 3B shows the valve in one of its open states.

DETAILED DESCRIPTION

Figure 1:
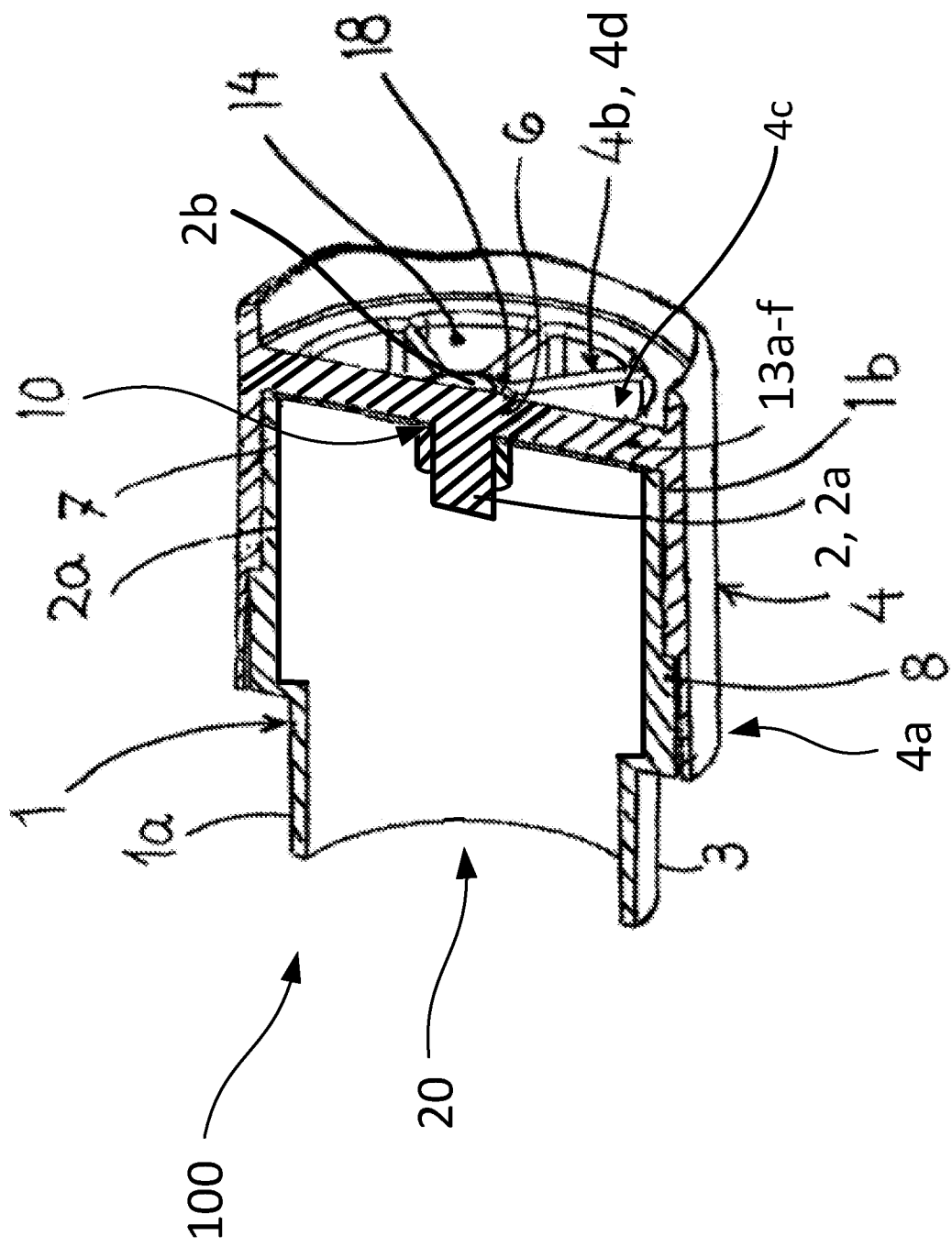
FIG. 1 is a three-dimensional longitudinal section of an embodiment of the tracheotomy valve according to the invention seen from a first angle of the outer side.
Figure 2:
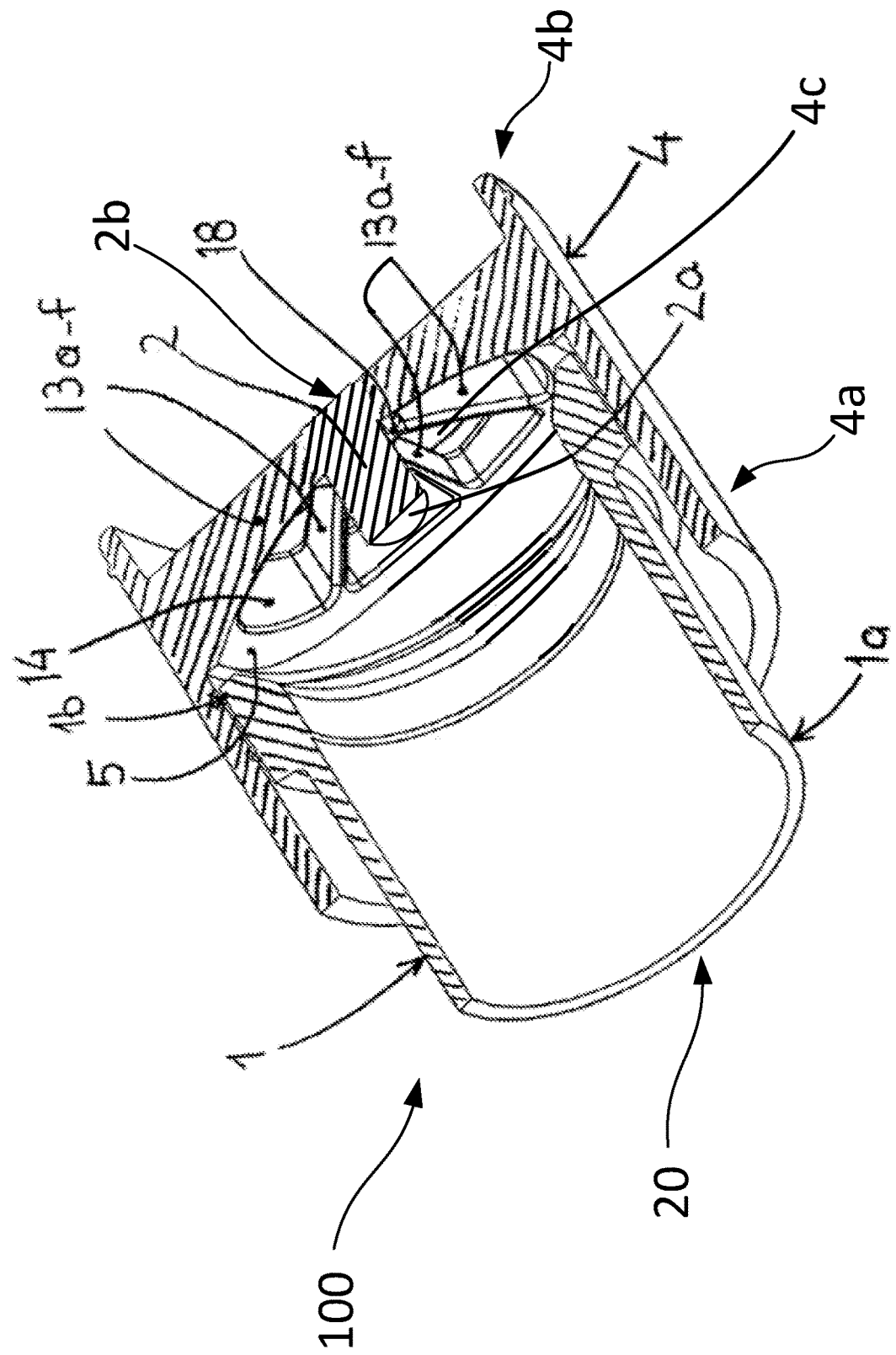
FIG. 2 is a three-dimensional longitudinal section of an embodiment of the tracheotomy valve according to the invention seen from a second angle of the inner side.

In the context of the present description and claims the expressions "inner" or "inwardly" indicate the part(s) or feature(s) being closest to, oriented towards or facing the patient. The expressions "outer" or "outwardly" indicate the part(s) being farthest away from, oriented away from or facing away from the patient when the valve is attached to a tracheotomy tube.

Aspects of the present disclosure will be described more fully hereinafter with reference to accompanying figures. The assembly disclosed herein can, however, be realized in many different forms and should not be construed as being limited to the aspects set forth herein.

The terminology used herein has the purpose of describing particular aspects of the disclosure only, and is not intended to limit disclosure. As used herein, singular forms "a", "an" and "the" are intended to include plural forms as well, unless the context clearly indicates otherwise.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A first preferred embodiment of the invention is shown in FIGS. 1-6. This embodiment comprises a tracheostomy valve 100 with a valve body 1 having two ends 1a, 1b. The valve body 1 comprises a first inner end 1a, a second outer end 1b, and a passageway 20 extending between the ends 1a, 1b through the valve body allowing air to flow from and through the first end 1a to and through the second end 1b, see also arrows 15 in FIGS. 3A and 3B visualising the airflow. The passageway 20 is circular in cross-section.

The outside of the inner end 1a is provided with a conical shape 3 to mate with a standard tracheotomy tube. A protrusion or post or pin 2 with a circular cross-section is arranged centrally and directed perpendicularly inwardly, i.e. pointing towards the inner end 1a, on an inner side or surface of a cap 4 that is configured to be attached detachably to the outer end 1b of the valve body 1. The valve 100 also comprises a flexible circular membrane 7 placed at an inner end 4a of the cap and between an inner surface 5 working as a seat on this inner cap end and the outer end 1b of the valve body 1. The flexible membrane 7 has a circular hole 10 at the centre having a diameter corresponding to the diameter of the post 2. The post 2 extends through the hole 10 in the membrane 7.

Figure 3A:
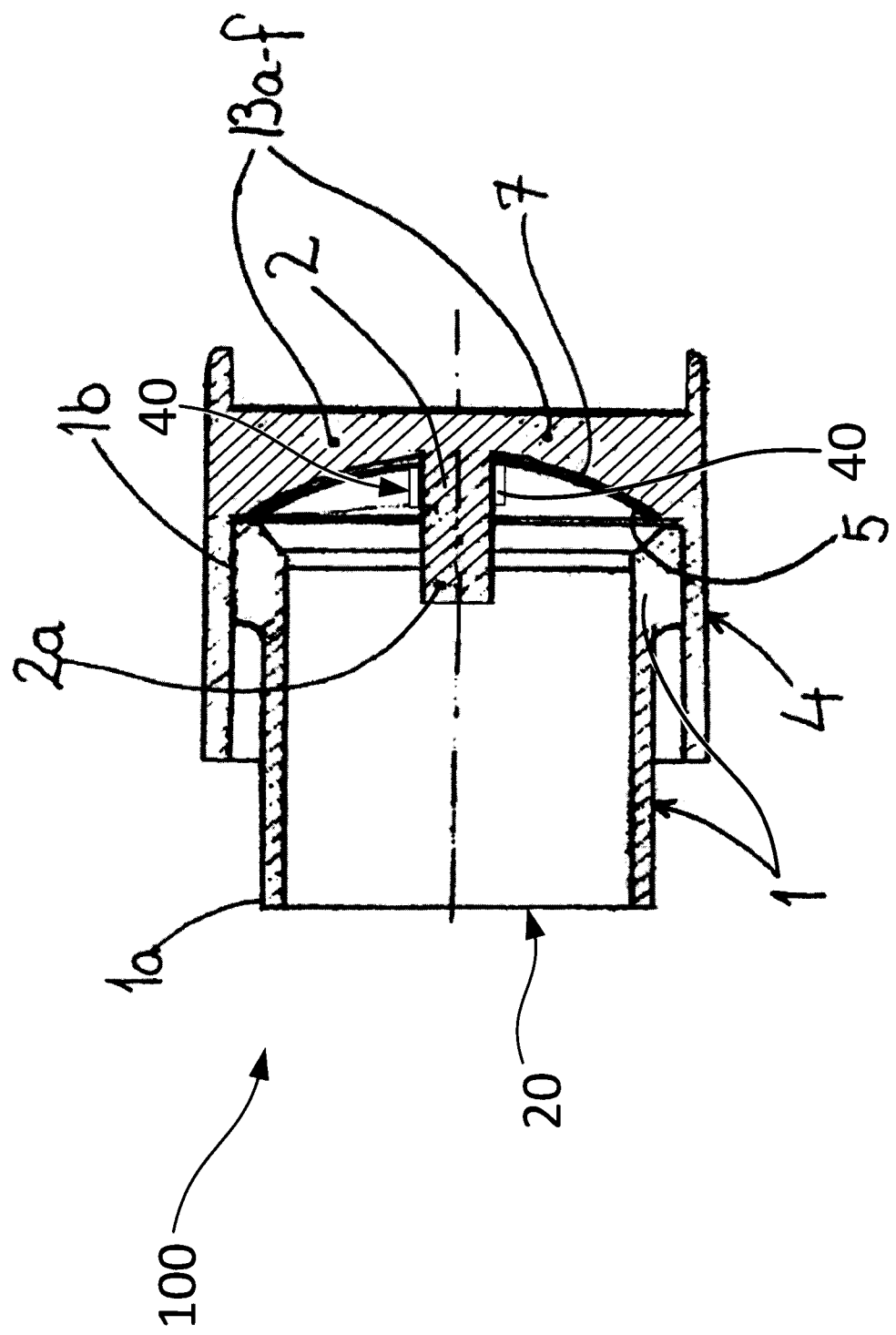
Figure 4:
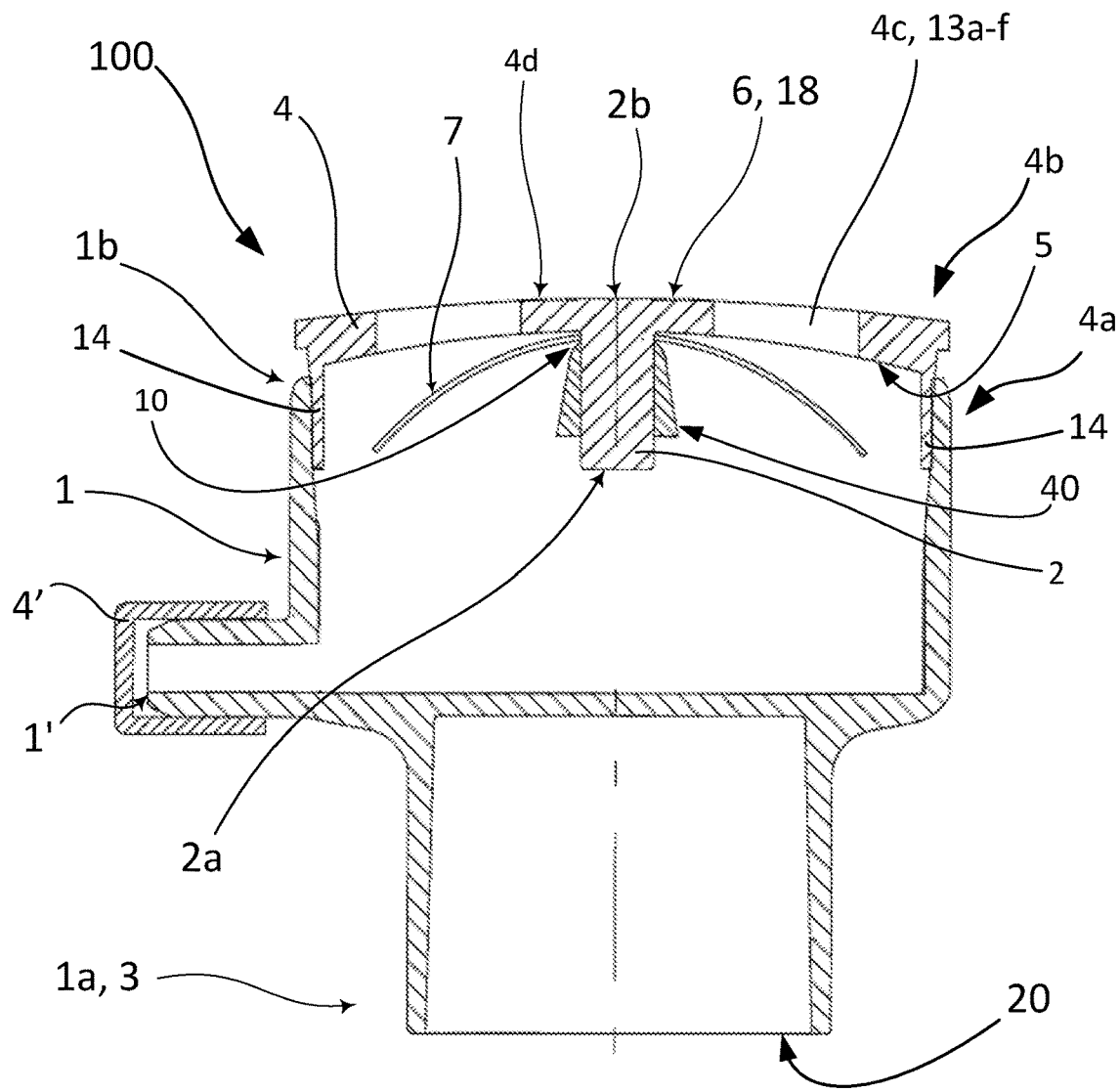
FIG. 4 is a planar section of one embodiment of the valve in FIGS. 1 to 3.
Figure 6:
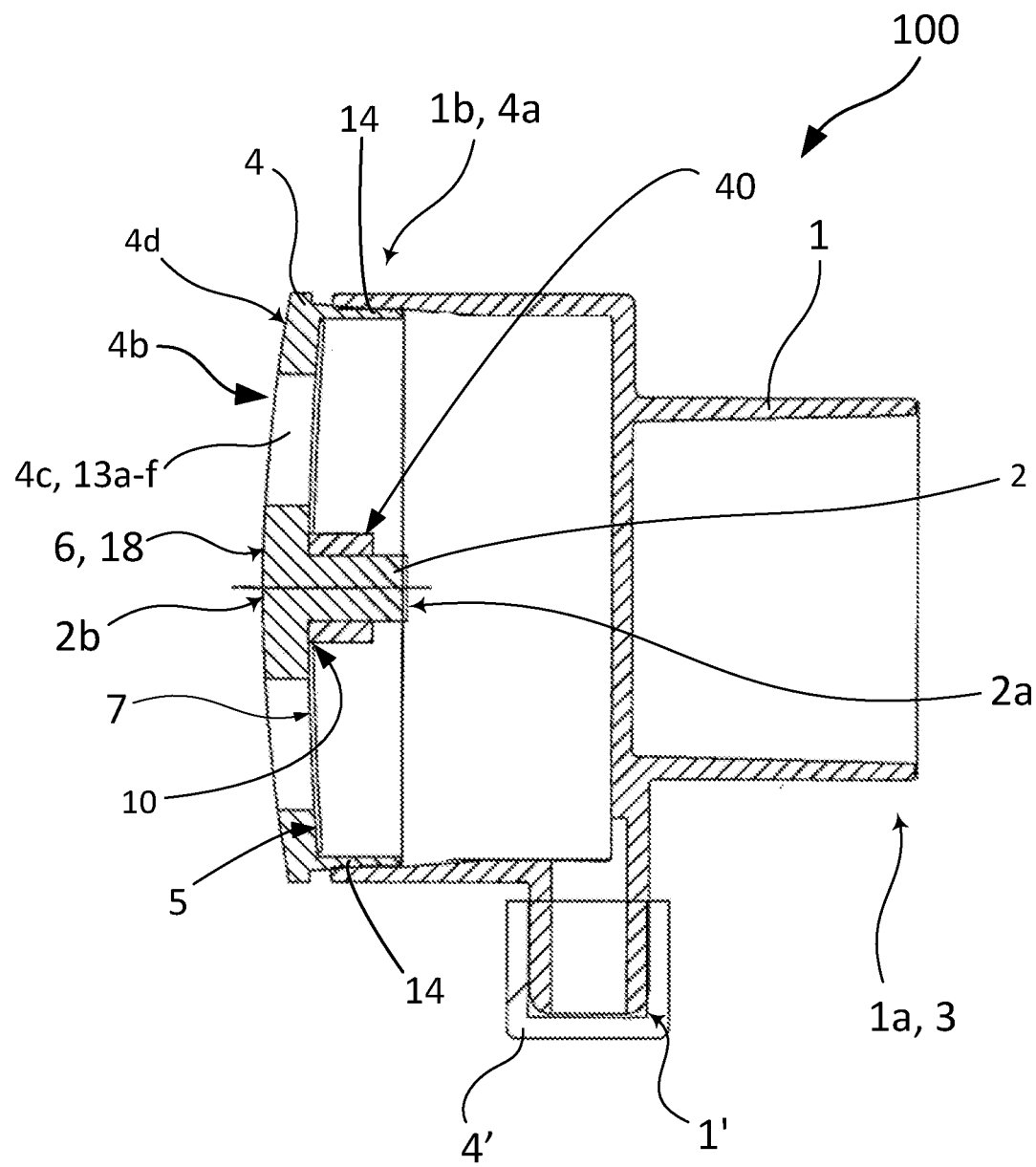
FIG. 6 is a section of another embodiment of the valve in FIGS. 1 to 3 but in a view turned 90° counter-clockwise compared to the view in FIG. 4.

The inner surface or passageway 20 of the valve 100 is substantially straight and planar as shown in FIGS. 1 to 3B, but is larger closer to the cap 4 as shown in FIGS. 4 and 6 due to a narrowing transcendence closer to the inner end 1a of the valve body 1, similar to an adapter that has a larger diameter at one end 1b and a smaller diameter at the other end 1a. However, these increasing and/or decreasing and/or maintained diameters along the length and airflow direction of the valve 100 is adapted for the desired application to and need of a patient.

The valve cap 4 is secured to the outer end 1b of the valve body 1. The cap 4 has a circular opening with a diameter largely corresponding to the inner diameter of the passageway 20. This opening has a circular rim 14. The cap 4 is provided with the post or pin 2 at a centre hub 18 forming an area or section 6 in the middle or centre of the cap. The inner surface 5 of the cap is not straight and/or planar.

Figure 7:
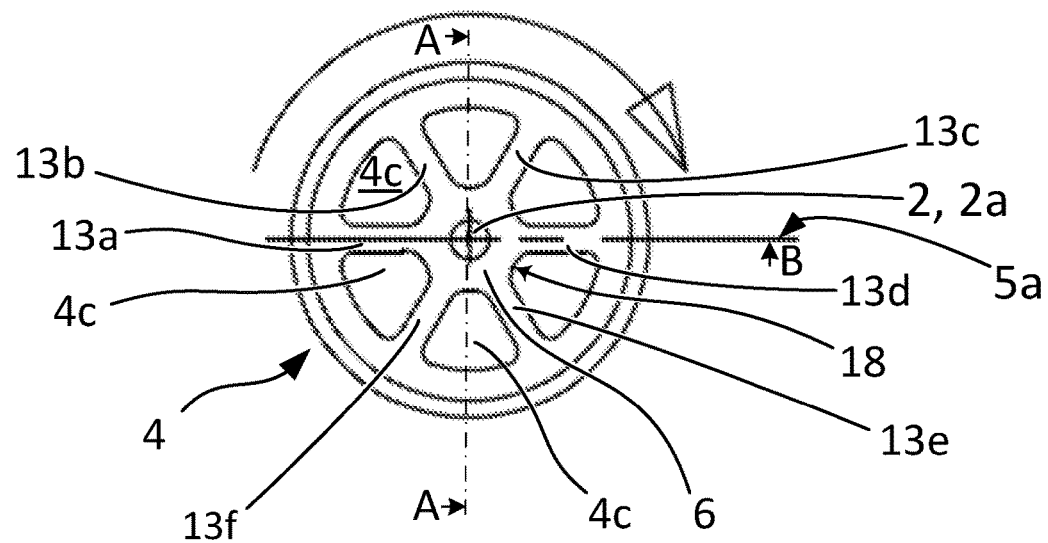
FIG. 7 shows the valve in FIG. 1 in planar view as seen from the right side to the left side in FIG. 1 in a direction in parallel with the centre axis and flow of air into or out of the valve.
Figures 8, 9:
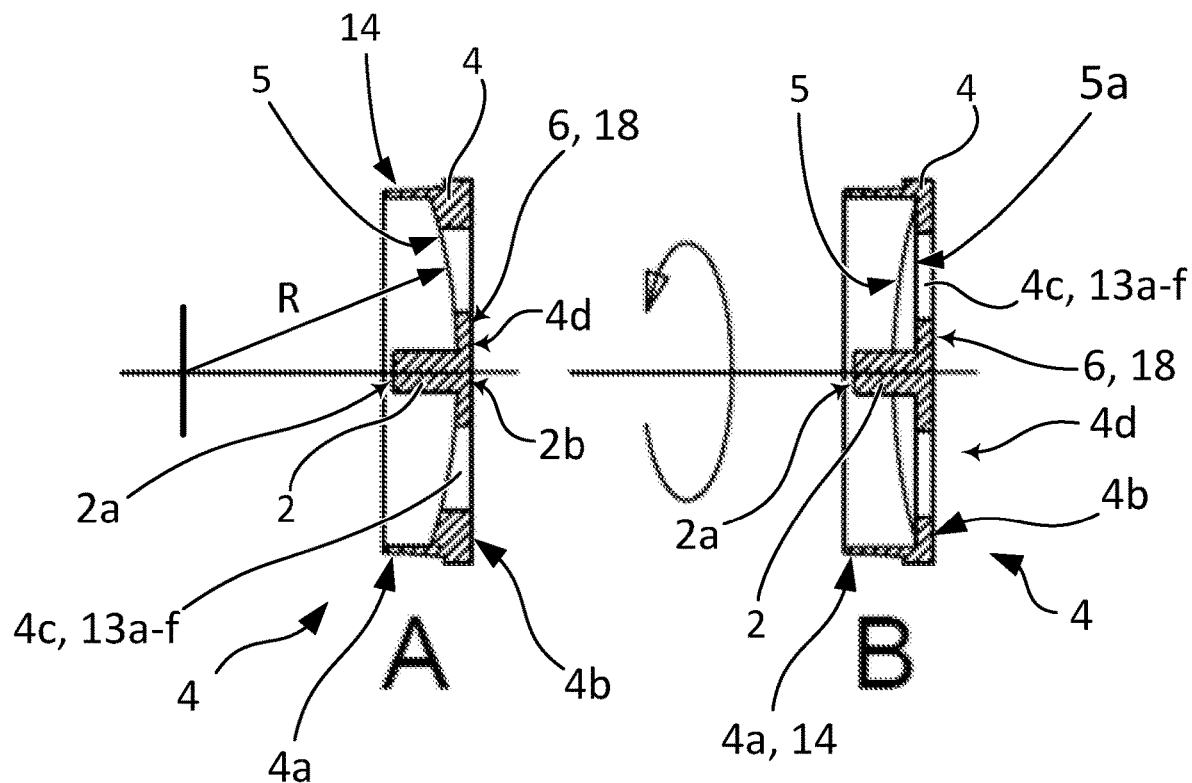
FIGS. 8 and 9 show the valve in section to reveal its shape of an inner surface against which an inner membrane is adapted to abut when the patient exhales or is not inhaling.

The cap 4 comprises at least one through hole 4c making the cap fenestrated to enable letting in air therethrough. The hollow valve body 1 has also a through hole forming the passageway 20 for fluid extending between the cap hole 4c and the inner end 1a being an outlet of the hollow valve body. The outer valve body end 1b is the inlet of the hollow valve body. The fenestrated cap and its inner end 4a face towards and are adapted to sealingly fit into the outer valve body end 1b when detachably attached thereto. The cap 4 of course comprises an outer end 4b facing in the opposite direction of the inner cap end 4. The inner cap end 4a has an opening defined by the circumferential rim 14 with a size largely corresponding to the inner size of the outer valve body end 1b. The cap centre hub 18 between which and the circumferential rim 14 the at least one through hole 4c is configured to form at least one spoke 13a-f extending between the centre hub and the circumferential rim. The one or more spokes 13a-f of the fenestrated cap 4 has the inner surface 5 as an under side facing towards the circumferential rim 14 and the inner cap end 4a but also the valve body 1 when the cap is attached thereto. This inner spoke surface 5 is rounded or bent in at least one plane of extension. This inner spoke surface 5 is curved in at least one plane of extension. This inner spoke surface 5 is formed with a radius R in at least one plane of extension, which radius R is measured from a starting point closer to the inner valve body end 1a than the outer valve body end 1b, see FIG. 8. This inner spoke surface 5 is curved in only one plane of extension, this being illustrated in FIGS. 7-9, such that its cross-section as shown in FIG. 8 (view A) is rounded or bent or has a radius R as measured from a starting point to the left in this figure, i.e. towards or at the inner valve body end 1a (as a cross-section along line A-A in FIG. 7). This means that, if the shown plane or drawing sheet of FIGS. 8 and 9 forms an X-Y-plane, a Z-axis extends out of or into this plane or the drawing sheet. Hence, in FIG. 8 (view A), the Z-axis is straight while the cross-section of the inner spoke surface 5 is curved and in FIG. 9 (view B corresponding to a cross-section taken along line B/5a in FIG. 7), the Y-axis is straight and also the cross-section of the inner spoke surface 5. FIG. 7 illustrates for better clarification of the shape of the two differing cross-sections of the cap 4 that the inner spoke surface 5 is rotated 90° from the view A or orientation in FIG. 8 to the view B or orientation in FIG. 9 (see also the arrows showing the directions of rotation of the cap 4 in FIGS. 7-9). The shape of the surface 5 in FIG. 8 could be seen as concave in relation to the rim 14 and first end 4a of the cap 4 in one plane. The shape of the surface formed by the spokes 13-13f and the area/section 6 of the centre hub 18 forming the exposed surface 4d of the cap 4 facing to the right in FIG. 9 could be rounded or curved or seen as concave in that direction, but is a plane or straight surface here. The surface 5 is not a concave spherical surface in this embodiment, see further explanation below. The fenestrated cap 4 and the flexible membrane 7 are configured to be detachably connected together to form a membrane and cap unit 30 (see FIG. 5) being adapted to sealingly fit into the outer valve body end 1b when detachably attached thereto.

The membrane and cap unit 30 comprises a detachable fastener 40 configured to securely clamp/hold/retain the flexible membrane 7 in fluid sealing abutment with the inner spoke surface 5 when the patient is not inhaling, i.e. exhales. This fastener 40 has an outer size or diameter being larger than the centre hole 10 of the membrane 7. Hence, the fastener 40 is configured to be slid over the post 2 (the membrane 7 first being slid over the post 2) and then push the membrane towards the inner surface 5 such that the membrane 7 is formed or bends into a corresponding rounded or curved shape sealingly fitting to the rounded/curved shape of the inner surface, see FIG. 3A. Thereby, the membrane 7 is pre-bent or preloaded or pre-flexed such that the inhaling of a patient is enhanced. The membrane 7 thus is held between the fastener 40 and the inner surface of the cap 4. The rim 14 is provided with the inner seating surface 5 along the inner periphery of the rim 14. The seating surface 5 faces inwardly towards the membrane 7 for supporting the periphery of the membrane. The cap 4 is provided with the central hub 18 in which the post 2 is formed. Ribs, i.e. the spokes 13a-f extend radially from the hub 18 to the rim 14. The post 2, the ribs 13a-f and the rim 14 thus form a grid.

The seating surface 5 of the cap 4 is arranged to coincide with the upper surface or face of the membrane 7 at a distance being the thickness of the membrane at the centre hub 18 but in air sealing contact at the periphery, i.e. at the rim 14, see FIG. 3A, when the patient exhales.

The inner surfaces (i.e. of the grid) of the cap 4 and the ribs 13a-f are curved such that the seating surface 5 merges smoothly and continuously with the inner surfaces of the ribs 13a-f and the hub 18 in only one plane shown in FIG. 8, while these surfaces in a direction or plane being perpendicular to the plane in FIG. 8 are not curved, i.e. they are instead straight in the other plane shown in FIG. 9. The inner surfaces of the radial ribs 13a-f, the seating surface 5 and the inner surface of the hub 18 (i.e. the inner surface of the grid of the cap 4) can be said to generally follow the surface of a rounded envelope that is curved in FIG. 8 except for the straight contact line/area 5a in FIG. 9 about which the membrane 7 flexes inwards when the patient inhales and flexes back into sealing contact when the patient exhales. Hence, the curved surface shown in FIG. 8 is similar to a shallow saddle-shape or blunt roof-like shape, i.e. a saddle- or roof-shape formed by a planar rounded or circular plate/disc bent with a radius R in only one plane into a saddle- or roof-shape. Hence, the saddle-shape of the inner cap surface 5 is in other words defined as a surface formed by bending a flat disc about/around a straight cylinder. The flat disc forming the surface 5 could be circular, elliptic, oval or egg-shaped.

Another embodiment of the surface defined by the inner sides the grid of the cap 4 could be a curved shape or periphery of a completely flexible circular membrane 7 placed on top of an external surface being a sphere or a dome, even though this is not shown here. The apex or highest point could then be located in the centre of the post 2 along the centre axis of the valve 100 at a height or distance corresponding to where the inner surface 5 "cuts" the post 2. In other embodiments, the inner shape of the grid of the cap 4 need not necessarily be spherical, e.g. a parabolic or hyperbolic shape could also be used as well as any other similar curve.

Each one of the ribs 13a-f and the seating surface 5 thus will support the membrane 7 along substantially its entire area/propagation. It should be noted that the membrane 7 has been left out in FIG. 2 in order to better illustrate the curved shapes of the inner side of the cap 4, of the inner surface of the ribs 13a-f and of the seating surface 5.

In FIG. 3, the valve 100 is shown in a closed state. The section is taken through the post 2. The membrane 7 pressed against the curved inner surface 5 is given a vaulted shape defined by the cap grid as described above. Since the membrane 7 normally is planar, the membrane, when mounted in the membrane and cap unit 30, is preloaded against the curved inside 5 of the cap grid and consequently into a positively closed and sealing position against at least a part of the seating surface 5 forming a ring-shaped airproof contact area at all times except when the patient inhales as the membrane 7 then is flexing inwards towards the trachea out of sealing engagement to enable inlet of air. The general curvature of the inner side 5 of the cap grid also will shape and hold the membrane 7 in such a way that the risk for any folds or wrinkles at the edge of the membrane is minimized. The membrane is flexed in a welldefined direction over substantial part of its area. The membrane 7 is in other words controlled in its movement by being bent like or similar to two wings or sections or segments being bent back and forth about either sides of a straight but non-existing virtual beam, i.e. the contact line 5a, when opening the valve 100 for intake of air.

Figure 5:
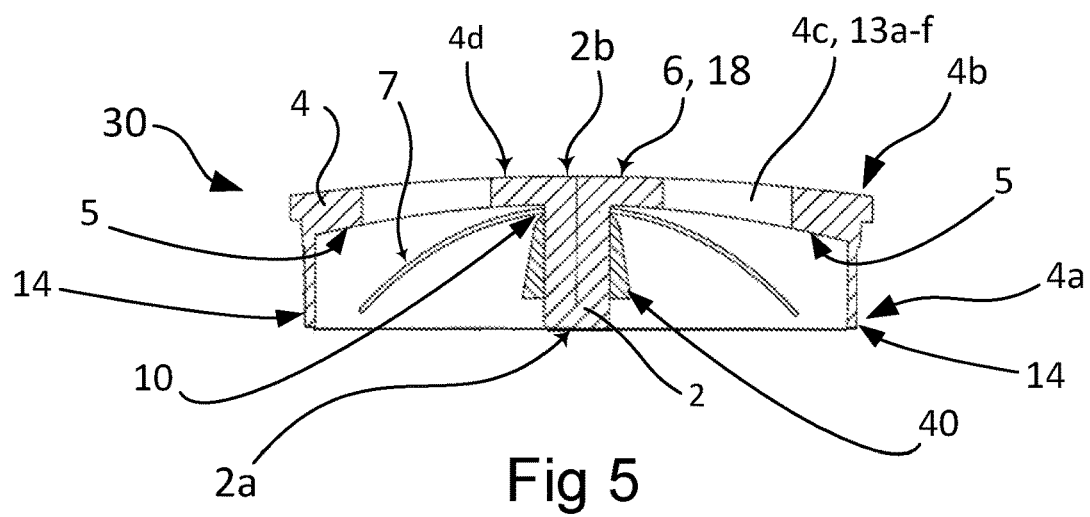
FIG. 5 is a section of another embodiment of the valve in FIGS. 1 to 3, i.e. in particular sub-parts assembled together as one unit as seen in FIG. 4.

In FIG. 4, the valve 100 is shown in the open state, i.e. when the patient inhales. The direction of the airflow is indicated by the arrows 15. This view is parallel to, but slightly offset from the section in FIG. 3 and consequently the post 2 and its end 2a can be seen in cross-section. As illustrated, the membrane 7 bends away from the seating surface 5 around the post 2. Since the detachable fastener 40 securely holds the membrane 7, the entire centre of the membrane will be held in contact with central hub 18. The edges of the fastener 40 thus will positively guide the flexing movement of the respective membrane segment. The first feature will minimize the influence of any folds, wrinkles or other irregularities in the membrane 7 and the second will minimize the risk for such folds, wrinkles or irregularities caused by clamping or otherwise constraining the membrane 7. This consequently means that the membrane 7 easily will open to the maximum extent possible. As indicated in FIG. 5, the edges of the outer surface of the fastener 40 preferably are rounded, which further will facilitate the flexing of the membrane 7 as well as improve the aerodynamic properties of the passageway 20. When the membrane flexes towards its closed position the membrane might progressively follow the curved grid from the central part 6, 18 to the seating ring 5, thus improving the noise characteristics.

Since the above embodiment is circular in cross-section, the valve body 1 and the cap 4 may be provided with orienting means ensuring that the grid and ribs 13a-f are located along each other when the valve 100 is assembled, e.g. if the membrane 7 has properties that in some orientations would hinder or improve its flexing or the airflow, such as a pattern or particular material of which it is manufactured. In one embodiment the orienting means comprise markings 8 located in one or several locations along the periphery.

In an alternative embodiment of the invention (not shown), the passageway 20 and the membrane 7 are generally elliptical in cross-section and the valve body 1 is adapted to conform to this shape. It should be noted that the valve 100 in common with tracheostomy valves in general also may be provided with connections for a ventilating machine and/or an oxygen supply and/or with filters and/or with a shower/heat shield, such as shown with an additional inlet 1' and a small cap 4' in FIGS. 4 and 6. The ribs 13a-f may be provided with a cross-section shaped as a narrow, symmetrical airfoil in order to improve the aerodynamics of the valve 100 when air 15 flow past them.

The person skilled in the art realizes that the present invention by no means is limited to the preferred embodiments described above. On the contrary, many modifications and variations are possible within the scope of the appended claims. For example, a valve 100 may comprise more than one, i.e. two or more passageways 20 and/or caps 4, i.e. one cap for each passageway, or flexible membranes 7, i.e. one for each passageway/cap, or the flexible membrane could be welded or glued with its centre, e.g. at least partly along/over the straight boundary or abutting/contacting line/area 5a or along/over the whole straight boundary or abutting line/area or contact line/area 5a shown in FIGS. 7 and 9, to the underside 5 of the hub 18 at the centre of the cap instead of being held or kept in place or securely clamped by a separate fastener 40. Alternatively, the fastener 40 could be permanently attached by some means, such as glue or welding or the like. However, the unit 30 formed by detachable connection of each cap 4 and membrane 7 is preferred as it can be stored as a spare part, and also eliminates having to handle separate and loose parts, i.e. a loose cap and a loose membrane that both are to be held when attached to the valve body 1. By pre-assembly of a cap 4 and membrane 7 into one unit 30, the number of parts to be handled is reduced. The detachable fastener 40 could likewise be threaded and threaded onto the cap 4 to sealingly seat/clamp the membrane 7 against the inner surface 5 of the cap.

The invention claimed is:

1. A tracheostomy valve configured to be in fluid communication with a patient's trachea, the tracheostomy valve comprising a hollow valve body, a flexible membrane adapted to work as a check valve opening the valve when the patient inhales and sealingly closing the valve when the patient exhales, and a cap with at least one through hole making the cap fenestrated, the hollow valve body having a through hole forming a passageway for fluid extending between an inner end being an outlet of the hollow valve body and an outer end being an inlet of the hollow valve body, wherein the fenestrated cap is configured to be detachably attached to the outer valve body end, and the inner valve body end is configured to be in fluid communication with the patient's trachea, the fenestrated cap comprising an inner end facing towards and adapted to sealingly fit into or onto the outer valve body end when detachably attached thereto and an outer end facing in the opposite direction of the inner cap end, the inner cap end having an opening defined by a circumferential rim with a size corresponding to an inner size of the outer valve body end, wherein the fenestrated cap comprises a center hub between which the circumferential rim and the at least one through hole is arranged forming at least one spoke extending between the center hub and the circumferential rim, wherein the at least one spoke of the fenestrated cap has an inner surface facing towards the circumferential rim and the inner cap end, wherein the inner spoke surface of the fenestrated cap is curved in only one plane of extension in a direction towards the outer cap end, and the fenestrated cap and the flexible membrane are configured to be detachably connected together to form a membrane and cap unit, wherein the membrane and cap unit is a standalone unit being adapted to sealingly fit into the outer valve body end when detachably attached thereto, wherein the membrane and cap unit comprises a detachable fastener configured to securely clamp the flexible membrane in fluid sealing abutment with the inner spoke surface of the fenestrated cap when the patient is not inhaling or exhales, wherein the center hub of the fenestrated cap comprises a protrusion extending from the center hub towards the inner cap end to a free end, and wherein the detachable fastener is configured to be slid/fitted over the center protrusion of the fenestrated cap when assembling the fenestrated cap and the flexible membrane together such that the flexible membrane is sealingly seated between the detachable fastener and the inner spoke surface of the fenestrated cap by being pushed by the detachable fastener towards the inner spoke surface of the fenestrated cap such that the flexible membrane is formed or bends into a corresponding curved shape sealingly fitting to the curved shape of the inner spoke surface of the fenestrated cap when the patient is not inhaling or exhales, and wherein the detachable fastener securely and detachably holds the flexible membrane such that center of the membrane is held in contact with the center hub of the fenestrated cap.

2. The tracheostomy valve according to claim 1, wherein the flexible membrane comprises a through hole in its center enabling sliding/fitting the flexible membrane over/around the center protrusion of the cap when assembling the cap and the flexible membrane together.

3. The tracheostomy valve according to claim 1, wherein the outer cap end comprises an exposed surface facing in the opposite direction of the inner spoke surface, which exposed surface is curved in the opposite direction of the inner spoke surface.

4. The tracheostomy valve according to claim 1, wherein the at least one spoke of the fenestrated cap has its inner spoke surface shaped with a curve outwards towards the outer cap end and an outer surface corresponding to an exposed surface of the outer cap end, which exposed cap surface faces in the opposite direction of the inner spoke surface and is shaped with a curve facing outwards.

5. The tracheostomy valve according to claim 1, wherein the at least one spoke of the fenestrated cap has its inner spoke surface shaped as a saddle/roof with its bent parts/sections/portions facing inwards towards the inner cap end.

6. The tracheostomy valve according to claim 1, wherein the inner spoke surface is shaped as the saddle/roof formed about/around/over a flat surface being curved in only one first plane, which flat surface extends straight in another plane perpendicular to the first plane.

* * * * *